US010544241B2

United States Patent
Henning et al.

(10) Patent No.: US 10,544,241 B2
(45) Date of Patent: *Jan. 28, 2020

(54) FARNESENE-BASED MACROMONOMERS AND METHODS OF MAKING AND USING THE SAME

(71) Applicant: Fina Technology, Inc., Houston, TX (US)

(72) Inventors: Steven K. Henning, Downingtown, PA (US); Taejun Yoo, Downingtown, PA (US); Herbert S. Chao, Paoli, PA (US)

(73) Assignee: Fina Technology, Inc., Houston, TX (US)

( * ) Notice: Subject to any disclaimer, the term of this patent is extended or adjusted under 35 U.S.C. 154(b) by 171 days.

This patent is subject to a terminal disclaimer.

(21) Appl. No.: 15/266,330

(22) Filed: Sep. 15, 2016

(65) Prior Publication Data

US 2018/0072826 A1 Mar. 15, 2018

(51) Int. Cl.
*C08F 36/22* (2006.01)
*A61K 8/81* (2006.01)
(Continued)

(52) U.S. Cl.
CPC ............ *C08F 36/22* (2013.01); *A61K 8/8152* (2013.01); *A61K 8/8194* (2013.01); *A61Q 19/00* (2013.01);
(Continued)

(58) Field of Classification Search
CPC ........ C08F 36/22; C08F 20/18; C08F 220/18; C08F 2500/17; C08F 2500/04;
(Continued)

(56) References Cited

U.S. PATENT DOCUMENTS

| 3,108,994 A | 10/1963 | Zelinski et al. |
| 3,210,333 A | 10/1965 | Strobel |

(Continued)

FOREIGN PATENT DOCUMENTS

| CA | 2837545 A1 | 4/2013 |
| CA | 2837547 A1 | 4/2013 |

(Continued)

OTHER PUBLICATIONS

International Search Report and Written Opinion for International Application No. PCT/US2017/049253, dated Dec. 14, 2017, 9 pages.

(Continued)

*Primary Examiner* — Taiwo Oladapo
(74) *Attorney, Agent, or Firm* — Albert Shung

(57) ABSTRACT

A macromonomer precursor is provided that includes a polymeric chain derived from farnesene and a single functional terminal end. The functional terminal end may include a hydroxyl group, an amino group, an epoxy group, an isocyanato group, or a carboxylic acid group. The terminal end of the macromonomer precursor may then be reacted with a (meth)acrylate to form a macromonomer having a (meth)acrylate functionalized terminal end that may be (co)polymerized with radically polymerizable monomers, such as alkyl(meth)acrylate monomers. Alternatively, a copolymer may be obtained by first deriving a poly(meth) acrylate from (meth)acrylate monomers having reactive groups that would allow the macromonomer precursors to be grafted onto the poly(meth)acrylate in a second step. The resulting copolymer may be incorporated as an additive in various formulations, such as a lubricant, a hydraulic fluid, a cosmetic composition, and an adhesive composition.

19 Claims, 3 Drawing Sheets

(51) Int. Cl.
*A61Q 19/00* (2006.01)
*C08F 20/18* (2006.01)
*C09J 133/10* (2006.01)
*C09J 147/00* (2006.01)
*C10M 145/14* (2006.01)
*C10N 40/08* (2006.01)

(52) U.S. Cl.
CPC ............ *C08F 20/18* (2013.01); *C09J 133/10* (2013.01); *C09J 147/00* (2013.01); *C10M 145/14* (2013.01); *A61K 2800/10* (2013.01); *C08F 2500/04* (2013.01); *C08F 2500/17* (2013.01); *C10M 2209/084* (2013.01); *C10N 2040/08* (2013.01)

(58) Field of Classification Search
CPC ....... C08F 136/22; C08C 19/38; C08C 19/44; C08G 81/021; C10M 145/14; C10M 2209/084; A61K 8/8194; A61K 8/8152; A61K 2800/10; C09J 147/00; C09J 133/10; A61Q 19/00; C10N 2040/08
See application file for complete search history.

(56) References Cited

U.S. PATENT DOCUMENTS

| | | |
|---|---|---|
| 3,897,514 A | 7/1975 | Allabashi |
| 5,338,588 A | 8/1994 | Billiu |
| 5,405,911 A | 4/1995 | Handlin, Jr. et al. |
| 5,565,130 A | 10/1996 | Omeis et al. |
| 5,587,433 A | 12/1996 | Boeckeler |
| 5,625,005 A | 4/1997 | Mallya et al. |
| 5,674,623 A | 10/1997 | Haddon et al. |
| 5,756,433 A | 5/1998 | Auschra et al. |
| 5,867,241 A | 2/1999 | Sampica et al. |
| 6,346,334 B1 | 2/2002 | Kamitani |
| 6,361,389 B1 | 3/2002 | Hogue et al. |
| 6,403,106 B1 | 6/2002 | Sebag et al. |
| 6,432,475 B1 | 8/2002 | Yamamoto et al. |
| 6,552,118 B2 | 4/2003 | Fujita et al. |
| 6,756,448 B2 | 6/2004 | Lee et al. |
| 7,192,688 B2 | 3/2007 | Klang et al. |
| 7,691,792 B1 | 4/2010 | Fisher et al. |
| 8,835,561 B2 | 9/2014 | Gandon-Pain et al. |
| 8,846,587 B2 | 9/2014 | DiBiase et al. |
| 9,012,385 B2 | 4/2015 | DiBiase et al. |
| 9,040,630 B2 | 5/2015 | McPhee |
| 9,175,242 B2 | 11/2015 | Radano et al. |
| 9,334,394 B1 | 5/2016 | Henning et al. |
| 9,752,027 B2 | 9/2017 | Sasaki et al. |
| 9,834,666 B2 | 12/2017 | Sasaki et al. |
| 2010/0190671 A1 | 7/2010 | Stoehr et al. |
| 2011/0319305 A1 | 12/2011 | Eisenberg et al. |
| 2012/0165474 A1 | 6/2012 | McPhee et al. |
| 2013/0079265 A1 | 3/2013 | Eisenberg et al. |
| 2014/0105838 A1 | 4/2014 | Farcet et al. |
| 2014/0138662 A1 | 5/2014 | Goeoetz et al. |
| 2014/0234553 A1 | 8/2014 | O'Hare et al. |
| 2014/0295150 A1 | 10/2014 | Bower et al. |
| 2014/0355117 A1 | 12/2014 | Bower et al. |
| 2015/0057392 A1 | 2/2015 | Koda et al. |
| 2015/0261368 A1 | 9/2015 | Chen |
| 2015/0284656 A1 | 10/2015 | Uehara et al. |
| 2016/0097017 A1 | 4/2016 | Eisenberg et al. |
| 2016/0137945 A1 | 5/2016 | Carrera et al. |
| 2016/0289502 A1 | 10/2016 | O'Hare et al. |
| 2018/0030194 A1 | 2/2018 | Uehara et al. |

FOREIGN PATENT DOCUMENTS

| | | | |
|---|---|---|---|
| CN | 1884328 A | 12/2006 | |
| CN | 103052664 A | 4/2013 | |
| CN | 104411734 A | 3/2015 | |
| EP | 2899255 A1 * | 7/2015 | ......... C10M 143/00 |
| EP | 2899255 A1 | 7/2015 | |
| JP | 07102017 A | 4/1995 | |
| JP | 2011132298 A | 7/2011 | |
| JP | 2015067805 A | 4/2015 | |
| JP | 2016-065221 A | 4/2016 | |
| JP | 2016-065222 A | 4/2016 | |
| JP | 2017014373 A | 1/2017 | |
| JP | 6442089 B2 | 12/2018 | |
| WO | 2008122593 A1 | 10/2008 | |
| WO | 2012018682 A1 | 2/2012 | |
| WO | 2013109834 A1 | 7/2013 | |
| WO | 2013173976 A1 | 11/2013 | |
| WO | 2013173977 A1 | 11/2013 | |
| WO | 2014029062 A1 | 2/2014 | |
| WO | 2014088936 A1 | 6/2014 | |
| WO | 2014088939 A1 | 6/2014 | |
| WO | 2014093014 A1 | 6/2014 | |
| WO | 2014142001 A1 | 9/2014 | |
| WO | 2014157624 A1 | 10/2014 | |
| WO | 2015045450 A1 | 4/2015 | |
| WO | 2015046524 A1 | 4/2015 | |
| WO | 2015046544 A1 | 4/2015 | |
| WO | 2016125899 A1 | 8/2016 | |
| WO | 2017003573 A1 | 1/2017 | |

OTHER PUBLICATIONS

Antkowiak et al., *J. Appl. Polymer Sci.*, 10:1319-34 (1972).
Berry and Fox, *Adv. Polym. Sci.*, 5:261-357 (1968).
Bueche, *J. Chem. Phys.*, 20(12):1959-64 (1952).
Dalsin et al., *ACS Macro Lett.*, 3, 423-427 (2014).
Duck, *Eur. Rubber J.*, 155(12):38-48 (1973).
Duck and Locke, *J. Inst. Rubber Ind.*, 2:223-227 (1968).
Foster and Binder, *Advances in Chemistry Series No. 19, Am. Chem. Soc.*, pp. 26-33 (1957).
Gruver and Krause, *J. Polym. Sci.*, 2, 797 (1964).
Hadjichristidis et al., *Chem. Rev.*, 101:3747-92 (2001).
Hsieh and Quirk, *Anionic Polymerization: Principals and Practical Applications*, Marcel Dekker, Inc., New York, pp. 92-127 (1996).
Kraus and Gruver, *J. Polym. Sci.*, 3:105-22 (1965).
Langer, *Polym. Preprints*, 7(1):132-39 (1966).
Makovetskii, et al. *Polymer Science, Ser. B*, 48:61-65 (2006).
Szwarc, *Nature*, 178:1168-69 (1956).
Szwarc et al., *J. Am. Chem. Soc.*, 78:2656-57 (1956).
Weissert and Johnson, *Rubber Chem. Tech.*, 40:590-601 (1967).
Canadian Office Action for Canadian Application No. 3,034,530, dated Apr. 11, 2019, 4 pages.
International Preliminary Report on Patentability for International Application No. PCT/US2017/049253, dated Mar. 19, 2019, 7 pages.
Non Final Office Action for U.S. Appl. No. 15/813,923, dated Sep. 24, 2018, 8 pages.
International Preliminary Report on Patentability for International Application No. PCT/US2016/033011, dated Jan. 2, 2018, 9 pages.
Notification of Reasons for Refusal for Korean Application No. 10-2018-7002838, dated Feb. 14, 2018, including English translation, 9 pages.
International Search Report and Written Opinion for International Application No. PCT/US2016/033011, dated Sep. 23, 2016—14 Pages.
Non Final Office Action for U.S. Appl. No. 14/753,449, dated Oct. 24, 2016, 12 pages.
Notice of Allowance for U.S. Appl. No. 14/753,449, dated Aug. 16, 2017, 8 pages.
Notice of Reasons for Rejection for Japanese Application No. 2017-568039, dated Jun. 29, 2018 with translation, 5 pages.
Final Office Action for U.S. Appl. No. 14/753,449, dated Jun. 2, 2017, 9 pages.
Non Final Office Action for U.S. Appl. No. 16/036,994, dated Aug. 27, 2018, 11 pages.
Korean Notification of Reason for Refusal for Korean Application No. 10-2019-7010684, dated Jun. 11, 2019 with translation, 11 pages.

(56) References Cited

OTHER PUBLICATIONS

Chinese Office Action for Chinese Application No. 201680039013.7, dated Sep. 5, 2018 with translation, 15 pages.
Notice of Reasons for Rejection for Japanese Application No. 2019-514241, dated Oct. 1, 2019, 9 pages.
English Translation of the Chinese Office Action for Chinese Application No. 201780056399.7, dated Oct. 16, 2019, 8 pages.

\* cited by examiner

FARNESENE-BASED MACROMONOMERS AND METHODS OF MAKING AND USING THE SAME

TECHNICAL FIELD

The present subject matter relates to macromonomers derived from polyfarnesene precursors that may be functionalized and then co-polymerized with radically polymerizable monomers, such as alkyl(meth)acrylates. Alternatively, the macromonomer precursors may be grafted onto a (co)polymer derived from radically polymerizable monomers. The resulting (co)polymers may be used in various formulations, such as lubricants, hydraulic fluids, cosmetics, and adhesives.

BACKGROUND

Macromonomers may be used to form comb or star shaped copolymers that are incorporated into compositions to enhance the properties of the composition. For example, the copolymer may include a polymeric backbone with a portion of the macromonomers forming side chains off of the backbone. The polymeric backbone may be derived from polar monomers, such as (meth)acrylates, while the macromonomers may be derived from non-polar monomers, such as butadiene or isoprene, that are polymerized and terminally functionalized. Examples of applications for such copolymers include viscosity index improvers for lubricant and hydraulic fluid compositions, water resistance additives for cosmetic compositions, and adhesion promoters in pressure sensitive adhesive compositions.

The macromonomers may be made by first manufacturing a precursor by anionic polymerization of a monomer, such as butadiene. Anionic polymerization allows for the control of the molecular weight, molecular weight distribution, and controlled reaction of the living chain ends. By controlling the macrostructure, rheological properties of the macromonomers can also be controlled. For example, it is known by those of skill in the art that molecular weight of the polymer is proportional to viscosity. Therefore, when a high molecular weight macromonomer is desired, the result may be a macromonomer of high viscosity that is difficult to process.

In many applications, consumers prefer that the macromonomer be provided in the form of a hydrogenated amorphous liquid. This may be accomplished by controlling the microstructure of the macromonomer and via hydrogenation. For example with respect to polybutadiene-based macromonomers, polar modifiers added to the solution for anionic polymerization, such as Lewis bases, are most often employed to control the level of vinyl structures in the resulting macromonomer. It has been reported that a minimum vinyl enchainment of 40% by weight is necessary to maintain a liquid, non-crystalline form for polybutadiene after hydrogenation.

Thus, there is a need for improved macromonomers and methods for obtaining macromonomers provided in the form of amorphous liquids that have relatively low viscosity for easier processing.

SUMMARY

According to one embodiment, a macromonomer precursor is provided that comprises a polymeric chain derived from farnesene and a single functional terminal end selected from a hydroxyl group, an amino group, an epoxy group, an isocyanato group, or a carboxylic acid group.

According to another embodiment, a copolymer is provided, wherein the copolymer is derived from monomers comprising radically polymerizable monomers and one or more macromonomers comprising a polymeric chain derived from farnesene and a (meth)acrylate functionalized terminal end. Various methods of obtaining the copolymer are also provided.

According to yet another embodiment, a copolymer is provided, wherein the copolymer is derived from first radically polymerizing (meth)acrylate monomers that include a reactive group to form a poly (meth)acrylate, and then reacting a macromonomer precursor in a second step with the reactive groups to graft the macromonomer precursor to the poly(meth)acrylate.

The copolymers may be incorporated in various formulations, such as lubricants, hydraulic fluids, cosmetics, or adhesives.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

DETAILED DESCRIPTION

Figure 1:
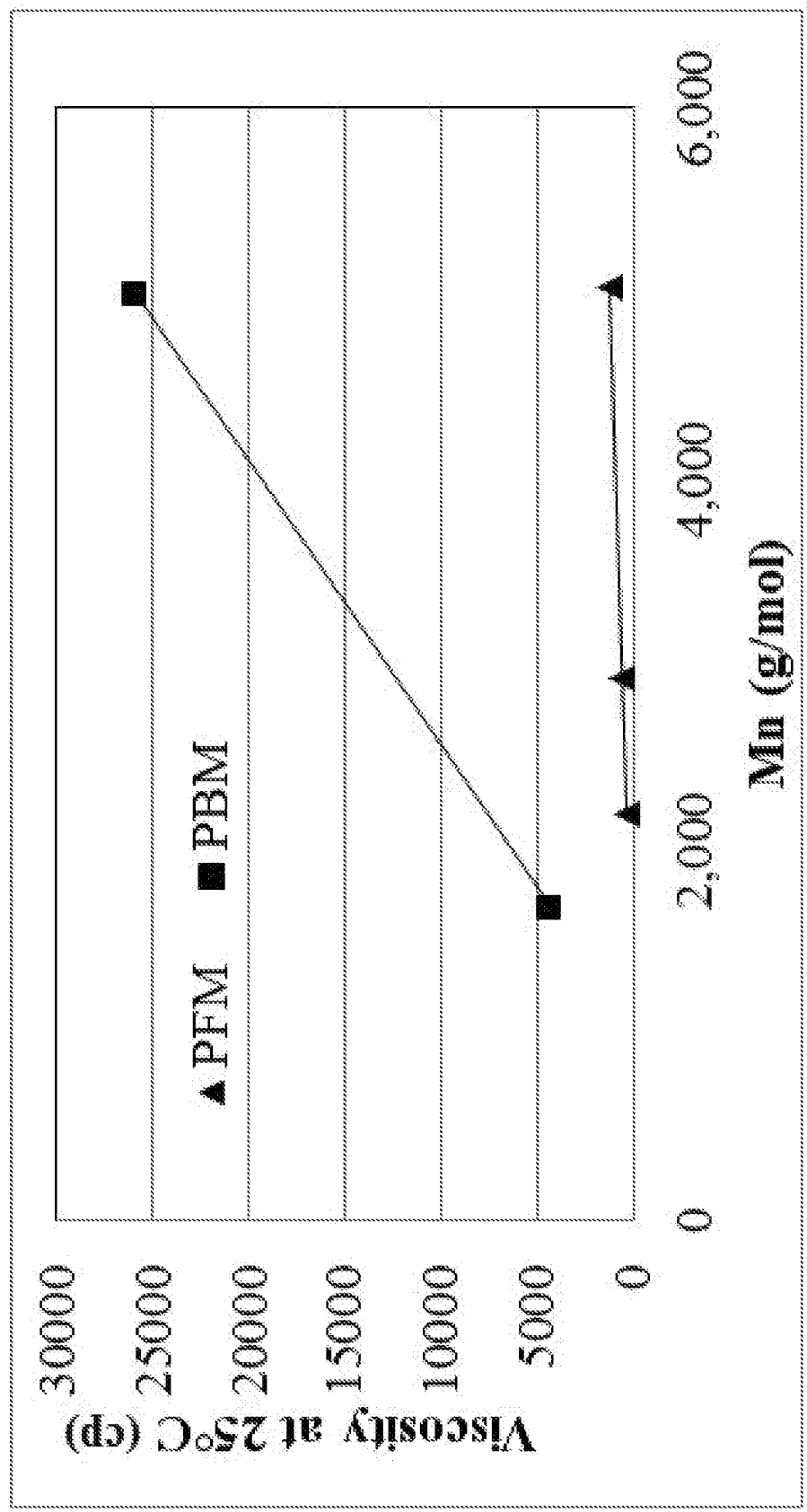
FIG. 1 is a plot of molecular weight vs. viscosity for samples of a macromonomer precursor as described herein compared to a polybutadiene macromonomer precursor.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, compounds, and/or compositions have been described at a relatively high-level, without detail, in order to avoid unnecessarily obscuring aspects of the present teachings.

As used herein, throughout the specification and the claims, "macromonomer" means a macromolecule that has one end-group which enables it to act as a monomer molecule, contributing only a single monomeric unit to a chain of a polymer or oligomer. Furthermore, as used herein, throughout the specification and the claims, "(co)polymer" means homopolymer or co-polymer, and "(meth)acrylate" means acrylate or methacrylate.

It has now been found that farnesene-based macromonomer precursors may be at least partially hydrogenated to form an amorphous liquid that exhibits very low viscosity as a function of molecular weight compared with diene-based macromonomer precursors, including those prepared from butadiene or isoprene. The macromonomer derived from these precursors also exhibit improved rheological properties. The practical result is that the macromonomer precursors and the macromonomers made therefrom remain liquid in form at molecular weights well above the molecular weight in which diene-based macromonomers, such as butadiene, become solid materials. In addition, the farnesene-based macromonomers exhibit low glass transition temperature (Tg) with decreased dependence on their microstructure. In contrast, butadiene-based macromonomers exhibit a range of Tgs depending on the amount of vinyl enchained in the backbone, as previously noted. Butadiene-based macromonomer precursors of low vinyl content that exhibit the same Tgs as the farnesene-based macromonomer precursors disclosed herein become semi-crystalline during hydrogenation, resulting in insoluble materials. Surprisingly, the low Tg, low 1,2 and 3,4 polymerization farnesene-based macromonomer precursors disclosed herein become an amorphous liquid even after hydrogenation.

According to the examples disclosed herein, farnesene-based macromonomers are provided that may be provided in the form of an amorphous liquid and exhibit much lower viscosity when compared to macromonomers based on dienes of equivalent molecular weight. The farnesene-based macromonomers may be derived from precursors in the form of an amorphous liquid exhibiting substantially lower viscosity than a diene-based precursor of equivalent molecular weight. The precursors may also be used similarly to the macromonomers by forming side chains grafted on the polymeric backbone of a (co)polymer. Thus, the macromonomer precursors disclosed herein may comprise a polymeric chain derived from farnesene; and a single functional terminal end selected from a hydroxyl group, an amino group, a carboxylic acid group, an isocyanato group, and an epoxy group.

Because of the lower inherent viscosity of the macromonomers disclosed herein, macromonomer formulations may be easily processed (e.g. mixed, coated, sprayed, etc.) without significant dilution with other components. The farnesene-based macromonomer may be used as the exclusive macromonomer or blended into compositions containing other macromonomers, such as diene-based macromonomers. The functional end-groups for the macromonomer may include a (meth)acrylate, which may be obtained from the macromonomer precursors having a hydroxyl end group, amino end group, epoxy end group, isocyanato group, or carboxylic acid end group, as described in greater detail below. The macromonomer precursors may be obtained by anionic polymerization of farnesene monomers alone or in combination with other monomers, such as dienes and vinyl aromatics.

Farnesene exists in isomer forms, such as α-farnesene ((E,E)-3,7,11-trimethyl-1,3,6,10-dodecatetraene) and β-farnesene (7,11-dimethyl-3-methylene-1,6,10-dodecatriene). As used in the specification and in the claims, "farnesene" means (E)-β-farnesene having the following structure:

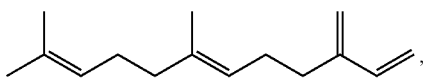

as well as (E)-β-farnesene in which one or more hydrogen atoms have been replaced by another atom or group of atoms (i.e. substituted).

The farnesene monomer used to produce various embodiments of the macromonomer precursor according to the disclosed methods and compositions may be prepared by chemical synthesis from petroleum resources, extracted from insects, such as Aphididae, or plants. Therefore, an advantage of the disclosed methods and compositions is that the precursor may be derived from a monomer obtained via a renewable resource. The monomer may be prepared by culturing a microorganism using a carbon source derived from a saccharide. The farnesene-based macromonomer precursor according to the disclosed methods and compositions may be efficiently prepared from the farnesene monomer obtained via these sources.

The saccharide used may be any of monosaccharides, disaccharides, and polysaccharides, or may be a combination thereof. Examples of monosaccharides include, without limitation, glucose, galactose, mannose, fructose, and ribose. Examples of disaccharides include, without limitation, sucrose, lactose, maltose, trehalose, and cellobiose. Examples of polysaccharides include, without limitation, starch, glycogen, and cellulose.

The cultured microorganism that consumes the carbon source may be any microorganism capable of producing farnesene through culturing. Examples thereof include eukaryotes, bacteria, and archaebacteria. Examples of eukaryotes include yeast and plants. The microorganism may be a transformant obtained by introducing a foreign gene into a host microorganism. The foreign gene is not particularly limited, and may be a foreign gene involved in the production of farnesene because it can improve the efficiency of producing farnesene.

In the case of recovering farnesene from the cultured microorganism, the microorganism may be collected by centrifugation and disrupted, and then farnesene can be extracted from the disrupted solution with a solvent. Such solvent extraction may appropriately be combined with any known purification process such as distillation.

Any methods known by those having skill in the art may be used to provide the farnesene-based macromonomer precursors described herein. Anionic polymerization may be desirable because anionic polymerization allows greater control over the final molecular weight of the precursor, i.e. narrow molecular weight distributions and predictable molecular weights. The living terminal end of the precursor may also be easily quenched, for example, by using an alkylene oxide followed by contact with a protic source providing a monol. As previously noted, the low viscosity farnesene-based macromonomers may be derived by polymerizing farnesene monomer alone or with at least one other monomer, such as butadiene or isoprene. For example, the macromonomer precursors made according to various embodiments of the disclosed methods and compositions are composed of at least 25 wt. % farnesene.

The farnesene-based macromonomer precursors described herein may be prepared by a continuous solution polymerization process wherein an initiator, monomers, and a suitable solvent are continuously added to a reactor vessel to form the desired precursor. Alternatively, the farnesene-based macromonomer precursors may be prepared by a batch process in which all of the initiator, monomers, and solvent are combined in the reactor together substantially simultaneously. Alternatively, the farnesene-based macromonomer precursors may be prepared by a semi-batch process in which all of the initiator and solvent are combined in the reactor together before a monomer feed is continuously metered into the reactor.

Initiators for providing a macromonomer precursor with a living terminal chain end include, but are not limited to, organic salts of alkali metals. The polymerization reaction temperature of the mixture in the reactor vessel may be maintained at a temperature of about −80 to 80° C.

As understood by those having skill in the art, living anionic polymerization may continue, as long as monomer is fed to the reaction. The farnesene-based macromonomer precursors may be obtained by polymerization of farnesene and one or more comonomers. Examples of comonomers include, but are not limited to, dienes, such as butadiene, isoprene, and myrcene, or vinyl aromatics, such as styrene and alpha methyl styrene. In one embodiment of the disclosed methods and compositions, a method of manufacturing a farnesene-based macromonomer precursor may comprise polymerizing a monomer feed, wherein the monomer feed comprises farnesene monomer and optionally at least one comonomer in which the comonomer content of the monomer feed is ≤75 wt. %, alternatively ≤50 wt. %, or alternatively ≤25 wt. %, based on the total weight of the monomer feed. The polymerization conditions and monomer feed may be controlled as may be desired so as to provide, for example, macromonomer precursors having a random, block or gradient structure.

The farnesene-based macromonomer precursors according to embodiments of the disclosed methods and compositions may have a number average molecular weight greater than or equal to 1,000 g/mol and less than or equal to 100,000 g/mol, alternatively less than or equal to 50,000 g/mol, as measured through a gel permeation chromatograph and converted using polystyrene calibration. The farnesene-based macromonomer precursors may have a viscosity less than or equal to 300,000 cP, alternatively less than 200,000 cP, or alternatively less than or equal to 30,000 cP, at 25° C.

Upon reaching a desired molecular weight, the macromonomer precursor may be obtained by quenching the living terminal end with a compound having the selected functionality or by providing the terminal end with a reactive group that may be subsequently functionalized. The macromonomer precursor, as noted previously, may be provided in the form of a polyfarnesene having either a hydroxyl, carboxylic acid, amino, isocyanato, or epoxy end group.

For the macromonomer precursor provided in the form of a polyfarnesene having a hydroxyl end group, anionic polymerization may be concluded by a quenching step in which the living terminal end of the polyfarnesene is reacted with an alkylene oxide, such as propylene oxide, and a protic source, such as an acid, resulting in a monol, i.e. a hydroxyl group on one of the terminal ends of the precursor.

In another example, the macromonomer precursor may be provided in the form of a polyfarnesene having a carboxylic acid end group. In one method, following anionic polymerization of farnesene monomers to provide a polyfarnesene chain having a living terminal end, the living terminal end may be contacted with carbon dioxide gas to provide the terminal end with a carboxylate followed by quenching the carboxylate with an acid, such as hydrochloric, phosphoric, or sulfuric acid to convert the carboxylate into a carboxylic acid. In another method, the carboxylic acid-terminated polyfarnesene may be obtained by reacting a polyfarnesene-based monol with a cyclic anhydride. Examples of cyclic anhydrides include, but are not limited to, phthalic anhydride, succinic anhydride, maleic anhydride, trimellitic anhydride, hexahydrophthalic anhydride, methyltetrahydrophthalic anhydride, itaconic anhydride, pyromellitic dianhydride, benzophenonetetracarboxylic dianhydride, and cyclopentanetetracarboxylic dianhydride.

In yet another example, the macromonomer precursor may be provided in the form of a polyfarnesene having an amino end group. In one method, a polyfarnesene based monol may be reacted with an alkane- or arenesulfonyl chloride or fluoride in the presence of a tertiary amine catalyst to form an alkane- or arenesulfonate terminated precursor. The alkane- or arenesulfonate terminated polymer may then be reacted with a primary amine or ammonia to provide the amine-terminated polyfarnesene macromonomer precursor.

Typical alkane- or arenesulfonyl compounds include, but are not limited to, methanesulfonyl chloride, methanesulfonyl fluoride, ethanesulfonyl chloride, ethanesulfonyl fluoride, p-toluenesulfonyl chloride, and p-toluenesulfonyl fluoride. Primary amines that may be reacted with the alkane- or arenesulfonate terminated polymer include, for example, ethylamine, propylamines, allylamine, n-amylamine, butylamines, cyclohexylamine, n-tetradecylamine, benzylamine, aniline, toluidines, naphthylamine and the like.

In an alternative method for producing an amine-terminated precursor, a polyfarnesene-based monol may be directly reacted with ammonia. For example, as explained above, the polyfarnesene-based monol may be provided by anionic polymerization of farnesene monomers in which the living terminal ends of the polymer are quenched using an epoxide followed by contact with a protic source. If the epoxide used is an alkylene oxide having the following structure:

in which R is a C1-C20 alkyl group, the resulting monol will be a secondary alcohol. The secondary hydroxyl-groups may then be reacted directly with ammonia in the presence of hydrogen and a catalyst under pressure (e.g. >2 MPa) to provide amine-terminated macromonomer precursors. A stoichiometric excess of ammonia with respect to the hydroxyl groups may be used. Examples of catalysts for the amination include, but are not limited to, copper, cobalt and/or nickel, and metal oxides. Suitable metal oxides include, but are not limited to, $Cr_2O_3$, $Fe_2O_3$ $ZrO_2$, $Al_2O_3$, and ZnO.

In yet another method, the macromonomer precursor having an amino end group may be obtained by adding acrylonitrile to either a primary or secondary OH end of a monol through Michael addition, followed by reduction to form a primary amino group at a terminal end. The polyfarnesene-based monol may be dissolved in an organic solvent and mixed with a base to catalyze the reaction. Examples of bases include, but are not limited to, alkali metal hydroxides and alkoxides, such as sodium hydroxide. Acyrlonitrile may then be added to the catalyst/monol mixture dropwise. The Michael addition of acrylonitrile (cyanoethylation) to the monol will form the corresponding cyanoalkylated compound.

In yet another example, the farnesene-based macromonomer precursor may be provided with an epoxy end group by, for example, a two-step process. In a first step, a polyfarnesene monol and a monoepoxy compound may be combined in a solvent and allowed to react under pressure or in the presence of an inert gas, such as nitrogen or a noble gas. Examples of monoepoxy compounds include epihalohydrins, such as epichlorohydrin, beta-methylepichlorohydrin and epibromohydrin. The reactants may be optionally mixed with a catalyst, such as a metal salt or semimetal salt, the metal being selected from boron, aluminium, zinc and tin, and at least one anion selected from F$^-$, Cl$^-$, BF$_4^-$, PF$_6^-$, AsF$_6^-$, SbF$_6^-$, ClO$_4^-$, IO$_4^-$, and NO$_3^-$. Following the first step, excess monoepoxy compound may be removed by distillation, for example, and then at least one alkali metal hydroxide may be added to the reaction mixture in order to form an alkali metal halide and the glycidyl-terminated precursor.

According to yet another example, the farnesene-based macromonomer precursor may be provided with an isocyanato end group. This may be accomplished by, for example, reacting a farnesene-based macromonomer precursor having an amino end group with phosgene.

As understood by one of skill in the art, the reactants used to provide the macromonomer precursors may be dissolved in a suitable organic solvent and heat and/or pressure may be applied to the reaction to promote formation of the macromonomer precursors. The reaction may be carried out batchwise or as a semicontinuous or continuous process. The reaction products may be recovered and treated by any conventional method, such as distillation, evaporation or fractionation to effect separation from unreacted material, solvent, if any, and by products.

The farnesene based macromonomer precursor may be at least partially saturated. As used herein throughout the specification and the claims, "partially saturated" means hydrogenated to decrease the degree of unsaturation of the macromonomer. In some examples, the degree of unsaturation may be less than or equal to 50%, alternatively less than or equal to 10%. The degree of unsaturation is equal to the ratio of the Iodine value after hydrogenation to the original Iodine value of the polymer prior to hydrogenation. Hydrogenation may be carried out by a variety of processes familiar to those of ordinary skill in the art including, but not limited to, hydrogenation in the presence of catalysts, such as Raney Nickel, noble metals, soluble transition metal catalysts, and titanium catalysts, for example.

Following hydrogenation, the precursor may be finally converted to a macromonomer by reacting the end-group of the precursor to obtain an at least partially saturated macromonomer having a (meth)acrylate end group. The (meth) acrylate end group may be obtained by a variety of methods. For example, direct acrylation may be achieved by reacting the terminal end of a precursor having a hydroxyl or amino end group with (meth)acrylic acid, (meth)acrylic ester, (meth)acrylic halide, or (meth)acrylic anhydride to form the (meth)acrylate-terminated macromonomer.

Alternatively, the precursors having a hydroxyl, carboxylic acid, amino, or epoxy end group may be reacted with an acrylated isocyanate compound, such that the isocyanate group reacts with the hydroxyl, carboxylic acid, epoxy, or amino end group of the precursor. For example, a precursor having a hydroxyl or carboxylic end group may be reacted directly with 2-isocyanatoethyl (meth)acrylate. In yet another example, the precursor having a hydroxyl, carboxylic acid, or amino end group may be esterified by reaction with the epoxy groups of glycidyl (meth)acrylate resulting in (meth)acrylate terminal ends. The acrylated isocyanate compound may be obtained by reacting an isocyanate-group containing compound having a functionality of at least 2 with a hydroxyl (meth)acrylate. The isocyanate-group containing compounds having a functionality of at least 2 include, but are not limited to, 4,4'-diphenylmethane diisocyanate (MDI), cyclohexanediisocyanate, p-phenylene diisocyanate, 1,5-naphthalene diisocyanate, toluene diisocyanate (TDI), p-xylene diisocyanate, hexamethylene diisocyanate, 4,4'-dicyclohexylmethane diisocyanate, 1,4-bis(isocyanomethyl)-cyclohexane, p-tetramethylxylene diisocyanate, m-tetramethylxylene diisocyanate, and isophorone diisocyanate. The hydroxyl (meth)acrylate may include any hydroxyalkyl (meth)acrylates, the alkyl group having 2 to 10 carbons, such as 2-hydroxyethyl acrylate.

In yet another example, the macromonomers may be obtained by reacting the precursors having an epoxy end group with (meth)acrylic acid, a hydroxyl (meth)acrylate, or an amino-alkyl (meth)acrylate.

The macromonomers having a (meth)acrylated terminal end may be copolymerized with one or more radically polymerizable monomers to form a (co)polymer. This may be achieved by free-radical polymerization of the macromonomers with the one or more radically polymerizable monomers.

In one example, the radically polymerizable monomers may comprise alkyl(meth)acrylate monomers having a structure according to formula (I):

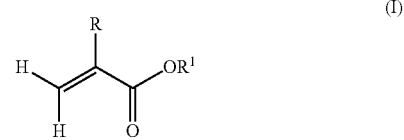

wherein R is hydrogen or methyl, and R$^1$ is a linear, branched or cyclic alkyl residue with 1 to 40 carbon atoms. In some examples, R$^1$ may be an optionally substituted hydrocarbyl in the form of a linear, branched or cyclic alkyl residue having 1 to 5 carbon atoms. Examples of monomers according to formula (I) are, among others, (meth)acrylates which derived from saturated alcohols such as methyl(meth) acrylate, ethyl(meth)acrylate, n-propyl(meth)acrylate, isopropyl(meth)acrylate, n-butyl(meth)acrylate, and tert-butyl (meth)acrylate. Preferably, the polymer comprises units being derived from methyl methacrylate.

The radically polymerizable monomers may also comprise a mixture of monomers comprising the alkyl(meth) acrylate monomers having a structure according to formula (I), as well as vinyl aromatics, such as styrene and α-methyl styrene, fumarates, maleates, vinyl esters, acrylonitriles, ethylene, 1,3-dienes, and combinations thereof.

The copolymer obtained from the polymerization of the macromonomer described above and the one or more radically polymerizable monomers may have a weight average molecular weight of from 5,000 to 1,000,000 g/mol.

The copolymer may be obtained by any known method, such as free-radical polymerization. Novel polymerization techniques such as ATRP (Atom Transfer Radical Polymerization) and or RAFT (Reversible Addition Fragmentation Chain Transfer) may alternatively be used to obtain the copolymers. Conventional radical initiators that may be used include azo initiators including but not limited to 2,2'-azodiisobutyronitrile (AIBN), 2,2'-azobis(2-methylbutyronitrile) and 1,1-azobiscyclohexane carbonitrile; peroxide compounds, e.g. methyl ethyl ketone peroxide, acetyl acetone peroxide, dilauryl peroxide, tert.-butyl per-2-ethyl hexanoate, ketone peroxide, methyl isobutyl ketone peroxide, cyclohexanone peroxide, dibenzoyl peroxide, tert.-butyl perbenzoate, tert.-butyl peroxy isopropyl carbonate, 2,5-bis (2-ethylhexanoyl-peroxy)-2,5-dimethyl hexane, tert.-butyl peroxy 2-ethyl hexanoate, tert.-butyl peroxy-3,5,5-trimethyl hexanoate, dicumene peroxide, 1,1-bis(tert.-butyl peroxy) cyclohexane, 1,1-bis(tert.-butyl peroxy) 3,3,5-trimethyl cyclohexane, cumene hydroperoxide and tert.-butyl hydroperoxide.

The polymerization may be conducted at any temperature and pressure, and the polymerization may be carried out with or without solvents, such as toluene, benzene and xylene, cyclohexane, heptane, octane, nonane, decane, dodecane, and mixtures thereof. Other solvents include mineral oils and synthetic oils (e.g. ester oils such as diisononyl adipate), and also mixtures thereof.

In an alternate method, the poly(meth)acrylate (co)polymer may be obtained in a first step before grafting the macromonomer precursors to the polymeric backbone of the (co)polymer in a second step. For example, a method of preparing a copolymer may comprise forming a poly(meth)acrylate by radically polymerizing one or more monomers according to formula (II):

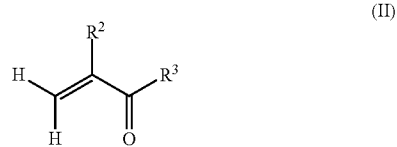

(II)

wherein $R^2$ is hydrogen or methyl, and $R^3$ is selected from the group consisting of a hydroxyl (i.e. to provide a carboxylic acid), a halogen, and —$OR^4$, wherein $R^4$ is an alcohol, an amino-alkyl, an isocyanato-alkyl, or an optionally substituted hydrocarbyl (such as a (meth)acrylate to form an anhydride). The one or more monomers may also comprise a mixture of monomers comprising the alkyl(meth)acrylate monomers having a structure according to formula (I), as well as vinyl aromatics, such as styrene and α-methyl styrene, fumarates, maleates, vinyl esters, acrylonitriles, ethylene, 1,3-dienes, and combinations thereof to form a (co)polymer. Depending on the functionality of the (co) polymers, one of the farnesene-based macromonomer precursors may be reacted with the poly(meth)acrylate to form polyfarnesene side chains on the polymeric backbone of the poly(meth)acrylate. For example, if the poly(meth)acrylate is the result of radically polymerizing (meth)acrylic acid, the acid groups along the polymeric backbone of the poly(meth)acrylate may be reacted with a farnesene-based macromonomer having a hydroxyl, amino, isocyanato, or epoxy end group. In another example, if the poly(meth)acrylate is the result of radically polymerizing hydroxyalkyl (meth)acrylate, the hydroxyl groups along the polymeric backbone of the poly(meth)acrylate may be reacted with a farnesene-based macromonomer having a carboxylic acid, isocyanato or epoxy end group.

The copolymers described herein may be incorporated into various compositions. For example, the copolymers may be combined with a base oil containing at least one of an ester oil and a hydrocarbon oil to form a lubricant composition. In other examples, the copolymers may be incorporated into hydraulic fluid compositions, cosmetic compositions, or adhesive compositions.

EXAMPLES

The advantageous properties of this invention can be observed by reference to the following examples, which illustrate but do not limit the invention.

Polyfarnesene Monol Synthesis

A polyfarnesene monol was prepared by combining 100 g of trans-β-farnesene and 200 g of methyl-tert-butyl ether (MTBE) in a pressure reactor and purged with nitrogen three times. Subsequently, 1.3 g of n-butyl lithium was added to the reactor at room temperature; the reaction was monitored and the temperature controlled to stay below 40° C. After polymerization was completed (approximately 15 minutes), a stoichiometric excess of propylene oxide (2.0 g) was added to the living polymerization solution, followed by adding methanol (1.3 g) for neutralization. The polymer solution was then transferred to a three-neck flask equipped with a stirrer, and mixed well for 10 minutes with purified water to wash the polymer solution. The stirring was stopped and over time the organic phase separated from the aqueous phase, at which point the aqueous phase was discharged and the pH determined. The washing step was repeated until the aqueous phase became neutral (pH=7). The separated organic phase was transferred to another three-neck flask and the MTBE solvent was removed under nitrogen purge with heating (150° C.). When the majority of solvent was removed, the polymer was steam stripped until one-half of the steam based on polymer volume was eliminated, then the polymer was nitrogen purged at 150° C. to pull out residual water. The isolated polyfarnesene macromonomer precursor having a hydroxyl end group was cooled to 70° C. and transferred to a container. The molecular weight of the polyfarnesene macromonomer precursor was approximately 5000 g/mol.

Hydrogenation 319 g of the polyfarnesene macromonomer precursor having a hydroxyl end group, 7.2 g of Ni catalyst and 336 g of heptane as a solvent were transferred to a pressure reactor, followed by three nitrogen purges. The reaction temperature was set to 100-130° under nitrogen pressure. Before reaching the boiling point of the solvent, the reaction mixture was purged with hydrogen another three times and hydrogen was continuously fed for the reaction. The reaction temperature was controlled by stirring speed and hydrogen pressure. In order to monitor the reaction, aliquots of sample were taken and FTIR was performed after drying the solvent, measuring the disappearance of peaks associated with residual unsaturation. This procedure was repeated until the peaks associated with unsaturated disappeared completely. After the reaction, the reaction mixture was cooled down to room temperature and the catalyst was removed by filtration. The final solution was stripped in a roto-evaporator under vacuum and the hydrogenated macromonomer precursor was isolated. The iodine value and hydroxyl value were determined from titration.

Acrylation

Urethane acrylates were prepared by reacting isophorone diisocyanate (IPDI) with 2-hydroxyethyl acrylate (HEA) to make acrylated isocyanate, and followed by reacting with the hydrogenated macromonomer precursor. 25 g of IPDI, 0.25 g of Irgonox 101 and 0.25 g of dibutyltin dilaurate (DBTDL) were transferred to a resin kettle equipped with a mechanical stirrer, thermocouple, dropping funnel and air spurge. 11.9 g of 2-hydroxyethyl acrylate (HEA) was continuously added to the reaction mixture at room temperature. The reaction temperature was 40° C. after compete addition. 0.17 g of Irgonox 1010 and 0.25 g of DBTDL was added to the reactor, and 125 g of hydrogenated macromonomer precursor was gradually added increasing the temperature to 70° C. An aliquot of reaction mixture was taken out to measure NCO value after 1 hour reaction. Additional hydrogenated macromonomer precursor was added until the NCO value fell below 1.0 mg KOH/g.

The polyfarnesene monol synthesis and hydrogenation methods were repeated to obtain samples of polyfarnesene of varying molecular weight. Comparative samples of polybutadiene monol and polyisoprene monol were prepared according to the same method, except that the trans-β-farnesene was replaced with either butadiene or isoprene. Molecular Characterization. Standard size exclusion chromatography (SEC) was utilized to determine molecular weight and molecular weight distributions of the polymer samples on an Agilent 1260 Infinity instrument in tetrahydrofuran (THF) using a guard column followed by two Agilent ResiPore columns in series with refractive index detection. Number and weight average molecular weight ($M_n$, $M_w$) and polydispersity ($M_w/M_n$) values for low molecular weight poly(butadienes) were determined using an in-house polybutadiene calibration curve. Low molecular weight polyisoprene and polyfarnesene values were determined using poly(styrene) calibration standards. While it is known that the choice of calibration standards can affect the reported molar mass, especially if structural differences between the calibration polymer and measured polymer exist, this technique has been chosen as it is a common practice.

$^1$H Nuclear Magnetic Resonance ($^1$H NMR) was used to determine the microstructure of poly(trans-β-farnesene) using a Bruker Avance III 400 MHz spectrometer with CDCl$_3$ as a solvent. Peak assignments for poly(trans-β-farnesene) have been reported in the literature. Fourier Transform Infrared Spectroscopy (FTIR) was performed on a Bruker Tensor 37 with an attenuated total reflectance attachment.

Thermal Properties.

Thermal properties of the samples were determined using a TA Instruments, Inc. DSC Q2000 differential scanning calorimeter. Samples were prepared in aluminum hermetically sealed pans, equilibrated at 100° C. for one minute, cooled, and subjected to a temperature ramp at 10° C./minute from −150° C. to 100° C. Glass transition ($T_g$) at the inflection point was recorded.

Viscosity.

Viscosity was measured by Brookfield viscometers, model DV-II+Pro and DV-II+viscometer at various temperatures.

Various samples of non-hydrogenated polyfarnesene macromonomer precursor having a hydroxyl end group of similar Tg, vinyl %, molecular weight, and viscosity at 25 C were compared to samples of non-hydrogenated polybutadiene macromonomer precursor having a hydroxyl end group of similar Tg and molecular weight. The results are provided in Table 1 and molecular weight vs. viscosity plotted in FIG. 1.

TABLE 1

| | Precursor Monomer | | | | |
|---|---|---|---|---|---|
| | Farnesene sample 1 | Farnesene sample 2 | Farnesene sample 3 | Butadiene sample A | Butadiene sample B |
| Mn (g/mol) | 2190 | 2920 | 5030 | 1700 | 5000 |
| Tg (° C.) | −57 | −55 | −62 | −56 | −57 |
| 1, 2/3, 4 content (%) | 40 | 40 | 40 | 65 | 65 |
| Visc @ 25 C. (cp) | 479 | 662 | 1355 | 4343 | 25997 |

In FIG. 1, the polyfarnesene macromonomer precursors having a hydroxyl end group exhibited a much lower viscosity than the butadiene-based macromonomer precursors having a hydroxyl end group of approximately the same molecular weight.

The viscosity of hydrogenated polybutadiene (PolyBd) vs. polyfarnesene (PolyFENE) macromonomer precursors having a hydroxyl end group was further investigated by comparing samples having different molecular weights. The results are provided in Table 2 with viscosity vs. temperature plotted on a logarithmic scale in FIG. 2.

TABLE 2

| | Sample | | | | |
|---|---|---|---|---|---|
| | HLBH5000M | HFENE20kM | HFENE5000M | HFENE35kM | HLBH1500M |
| Type | PolyBd | PolyFENE | PolyFENE | PolyFENE | PolyBd |
| Mn (g/mol) | 5000 | 20000 | 5000 | 35000 | 1500 |
| Temp (° C.) | | | Viscosity (cp) | | |
| 25 | 64,686 | 49,677 | 8,158 | 129,000 | 13,397 |
| 35 | 25,745 | 22,395 | 3,499 | 57,175 | 5,179 |
| 45 | 11,857 | 11,018 | 1,710 | 28,244 | 2,235 |
| 55 | 5,879 | 5,879 | 917 | 14,997 | 1,085 |
| 65 | 3,189 | 3,359 | 530 | 8,561 | 570 |
| 75 | 1,727 | 1,910 | | 4725 | |
| 85 | 1,067 | 1,215 | | 3020 | |
| 95 | 690 | 815 | | 2025 | |

Figure 2:
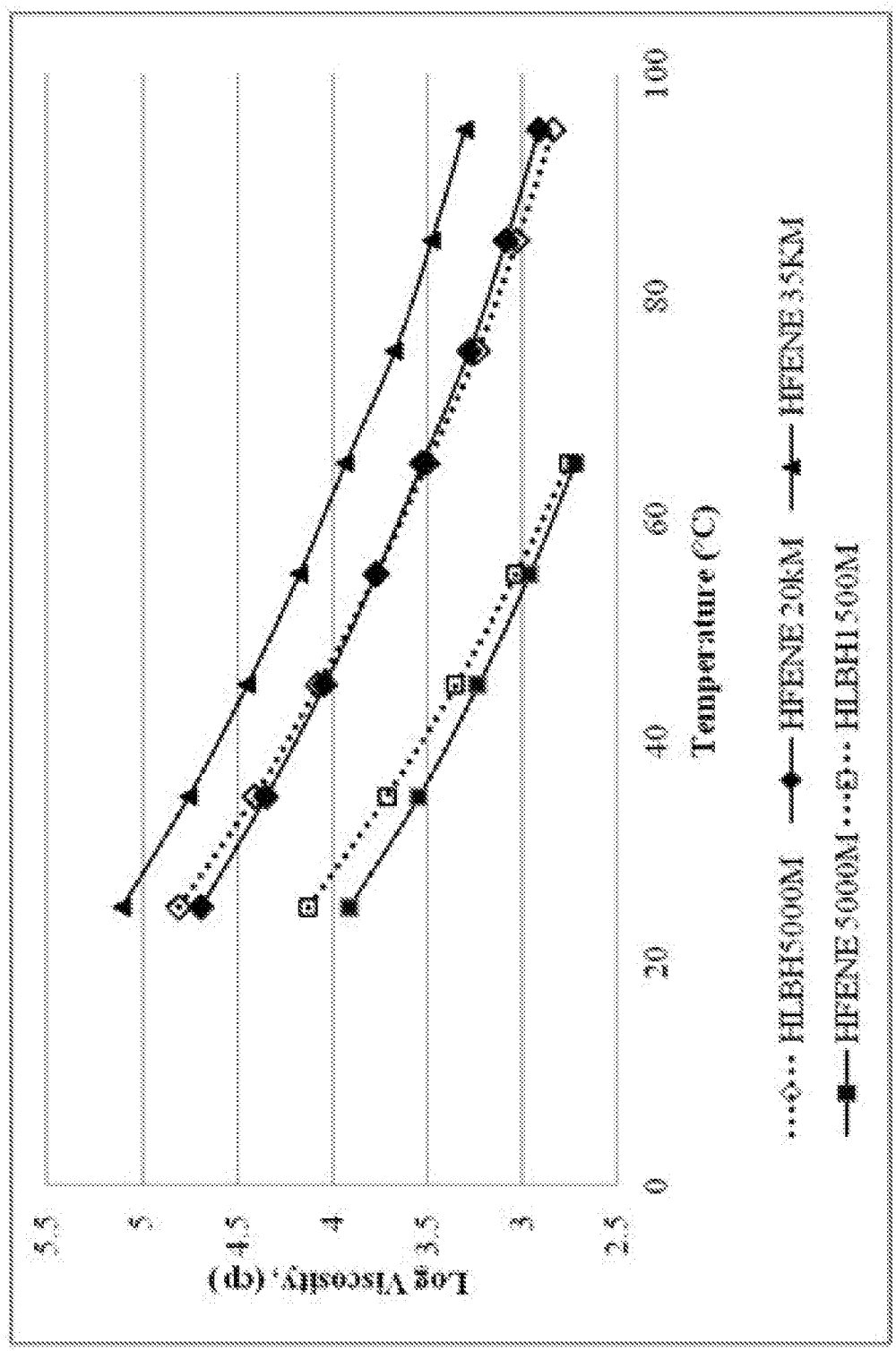
FIG. 2 is a plot of temperature vs. viscosity for samples of a macromonomer precursor as described herein compared to a polybutadiene macromonomer precursor.

FIG. 2 demonstrates that the polyfarnesene macromonomer precursors having a hydroxyl end group may exhibit approximately the same viscosity as a polybutadiene macromonomer precursor having a hydroxyl end group, despite having three to four times the molecular weight of the polybutadiene macromonomer precursor.

Additional samples of unfunctionalized polymers of farnesene, butadiene, and isoprene were prepared to determine the relationship between 1,2/3,4 content and Tg. The results are provided in Table 3 and vinyl content vs. Tg plotted in FIG. 3.

TABLE 3

| Type | Mn (g/mol) | Polydispersity Index | 1, 2/3, 4 Content (%) | Tg (° C.) |
|---|---|---|---|---|
| Polybutadiene 1 | 4,300 | 1.1 | 28 | −84 |
| Polybutadiene 2 | 3,900 | 1.1 | 70 | −40 |
| Polybutadiene 3 | 4,700 | 1.1 | 85 | −28 |
| Polybutadiene 4 | 5,200 | 1.1 | 90 | −15 |
| Polyisoprene 1 | 3,190 | 1.35 | 9 | −67 |
| Polyisoprene 2 | 2,470 | 1.25 | 56 | −32 |
| Polyisoprene 3 | 2,820 | 1.32 | 73 | −8 |
| Polyisoprene 4 | 3,110 | 1.59 | 85 | 0 |

TABLE 3-continued

| Type | Mn (g/mol) | Polydispersity Index | 1, 2/3, 4 Content (%) | Tg (° C.) |
|---|---|---|---|---|
| Polyfarnesene 1 | 10,370 | 1.23 | 9 | −75 |
| Polyfarnesene 2 | 10,650 | 1.19 | 39 | −73 |
| Polyfarnesene 3 | 10,580 | 1.05 | 52 | −70 |

Figure 3:
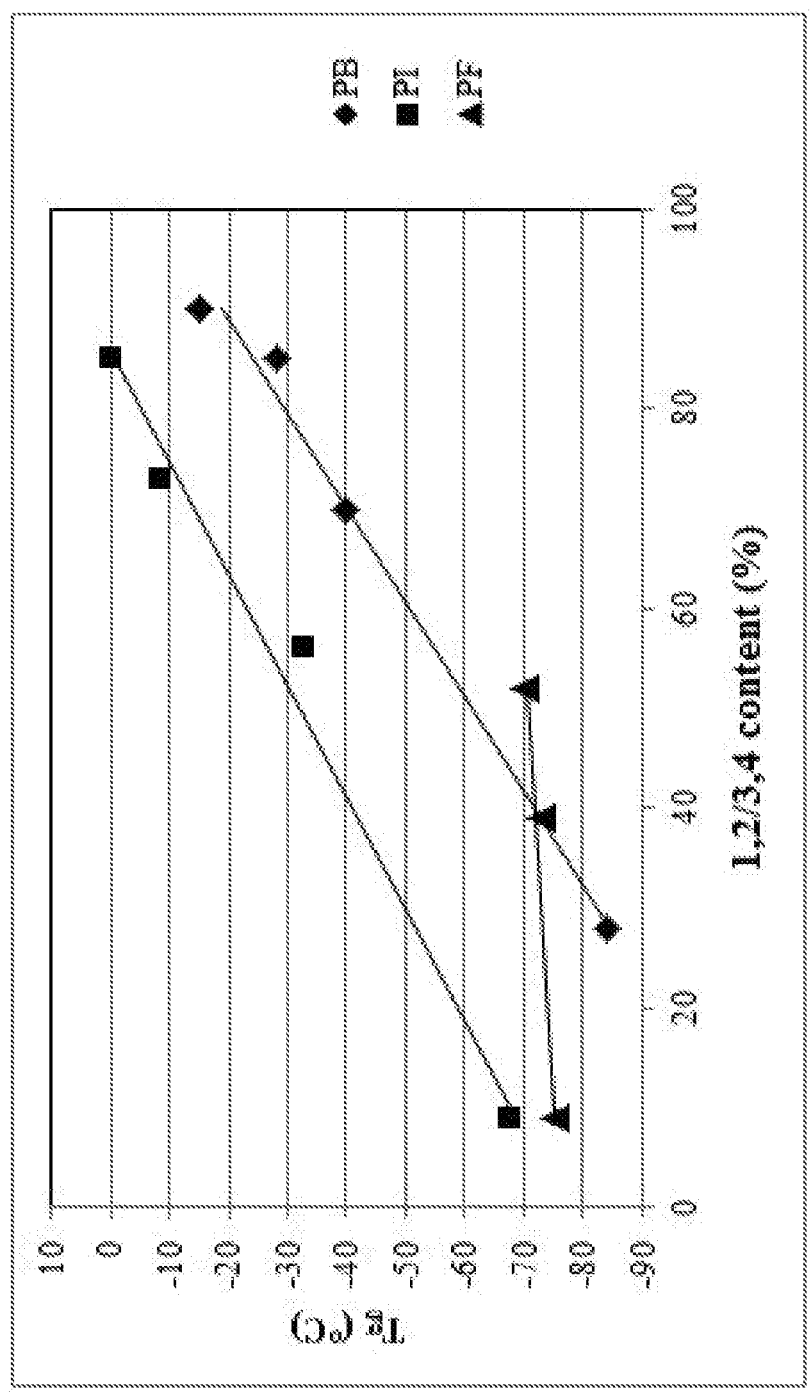
FIG. 3 is a plot of Tg vs. 1,2/3,4 content for samples of polyfarnesene, polybutadiene, and polyisoprene.

In FIG. 3, the slope of the plots of 1,2/3,4 content vs. Tg for the polyfarnesene macromonomer precursors having a hydroxyl end group is less that the slope of the similar plots for the polybutadiene and polyisoprene macromonomer precursors having a hydroxyl end group. This indicates that 1,2/3,4 content has much less effect on the Tg for the polyfarnesene macromonomer precursors.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entitles or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element. The terms "and" and "or" may have both conjunctive and disjunctive meanings.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

We claim:

1. A macromonomer precursor consisting of:
a polymeric chain derived from monomers consisting of farnesene and, optionally, at least one diene;
wherein the polymeric chain has terminal ends and wherein only one of the terminal ends is functionalized with a hydroxyl group, an amino group, an epoxy group, an isocyanato group, or a carboxylic acid group.

2. The macromonomer precursor of claim 1, wherein the polymeric chain has been hydrogenated and a degree of unsaturation less than or equal to 10% and wherein degree of unsaturation is equal to the ratio of the Iodine value after hydrogenation to the Iodine value before hydrogenation.

3. The macromonomer precursor of claim 1, wherein the farnesene comprises at least 25 wt. % of the macromonomer precursor.

4. The macromonomer precursor of claim 1 having a weight average molecular weight of from 1,000 to 100,000.

5. The macromonomer precursor of claim 1, wherein the polymeric chain is derived solely from farnesene.

6. A method of preparing a copolymer comprising:
reacting a macromonomer precursor according to claim 1 with a reactant according to formula (II):

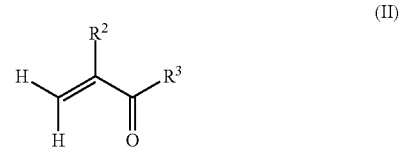

(II)

wherein $R^2$ is hydrogen or methyl, and $R^3$ is selected from the group consisting of a hydroxyl, a halogen, and —$OR^4$, wherein $R^4$ is a substituted hydrocarbyl to provide a (meth)acrylate terminated polyfarnesene macromonomer; and
copolymerizing the (meth)acrylate terminated polyfarnesene macromonomer with one or more radically polymerizable monomers.

7. The method of claim 6, wherein the macromonomer precursor is at least partially saturated prior to the reacting step.

8. The method of claim 6, wherein the optionally substituted hydrocarbyl is a linear, branched or cyclic alkyl residue having 1 to 5 carbon atoms.

9. A method of preparing a copolymer comprising:
reacting a macromonomer precursor according to claim 1 which is functionalized with a hydroxyl group, an amino group, or a carboxylic acid group with glycidyl (meth)acrylate to provide a (meth)acrylate terminated polyfarnesene macromonomer; and
copolymerizing the (meth)acrylate terminated polyfarnesene macromonomer with one or more radically polymerizable monomers.

10. The method of claim 9, wherein the macromonomer precursor is at least partially saturated prior to the reacting step.

11. A method of preparing a copolymer comprising:
reacting a macromonomer precursor according to claim 1 which is functionalized with a hydroxyl group, an amino group, an epoxy group, or a carboxylic acid group with an acrylated isocyanate compound to provide a (meth)acrylate terminated polyfarnesene macromonomer; and
copolymerizing the (meth)acrylate terminated polyfarnesene macromonomer with one or more radically polymerizable monomers.

12. The method of claim 11, wherein the macromonomer precursor is at least partially saturated prior to the reacting step.

13. A method of preparing a copolymer comprising:
radically polymerizing monomers according to formula (II) to form a poly(meth)acrylate:

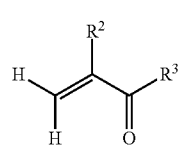

(II)

wherein $R^2$ is hydrogen or methyl, and $R^3$ is selected from the group consisting of a hydroxyl, a halogen, and —$OR^4$, wherein $R^4$ is an alcohol, an amino-alkyl, an isocyanato alkyl, or an optionally substituted hydrocarbyl; and reacting the poly(meth)acrylate with the macromonomer precursor of claim 1.

14. The method of preparing a copolymer according to claim 13, wherein the monomers according to formula (II) are radically polymerized with monomers selected from the group consisting of vinyl aromatics, fumarates, maleates, vinyl esters, acrylonitriles, ethylene, and combinations thereof.

15. A copolymer made according to claim 13.

16. A lubricant composition comprising
base oil containing at least one of an ester oil and a hydrocarbon oil; and
the copolymer of claim 15.

17. A hydraulic fluid composition comprising the copolymer of claim 15.

18. A cosmetic composition comprising the copolymer of claim 15.

19. An adhesive composition comprising the copolymer of claim 15.

\* \* \* \* \*